(12) United States Patent
Hebert et al.

(10) Patent No.: US 8,045,169 B2
(45) Date of Patent: Oct. 25, 2011

(54) METHOD AND DEVICE FOR MEASURING REFLECTED OPTICAL RADIATION

(75) Inventors: Raymond T. Hebert, Los Gatos, CA (US); Joel M. Blatt, Palo Alto, CA (US); Joseph T. Widunas, Fremont, CA (US)

(73) Assignee: Bayer HealthCare LLC, Tarrytown, NY (US)

( * ) Notice: Subject to any disclaimer, the term of this patent is extended or adjusted under 35 U.S.C. 154(b) by 0 days.

(21) Appl. No.: 12/235,371

(22) Filed: Sep. 22, 2008

(65) Prior Publication Data

US 2009/0027682 A1      Jan. 29, 2009

(51) Int. Cl.
G01N 21/55      (2006.01)

(52) U.S. Cl. ......................................... 356/445; 356/448

(58) Field of Classification Search .................. None
See application file for complete search history.

(56) References Cited

U.S. PATENT DOCUMENTS

| | | | |
|---|---|---|---|
| 3,536,927 A | 10/1970 | Mink et al. | |
| 4,219,529 A | 8/1980 | Tersteeg et al. | |
| 4,224,032 A | 9/1980 | Glover et al. | |
| 4,518,529 A | 5/1985 | Imada et al. | |
| 4,676,653 A | 6/1987 | Strohmeier et al. | |
| 4,756,619 A | 7/1988 | Gerlinger et al. | |
| 4,791,461 A * | 12/1988 | Kishimoto et al. | 356/446 |
| 5,064,619 A * | 11/1991 | Finlan | 356/445 |
| 5,078,497 A | 1/1992 | Borton et al. | |
| 5,442,435 A * | 8/1995 | Cooper et al. | 356/133 |
| 5,467,778 A | 11/1995 | Catt et al. | |
| 5,526,120 A | 6/1996 | Jina et al. | |
| 5,701,181 A | 12/1997 | Boiarski et al. | |
| 5,728,352 A | 3/1998 | Poto et al. | |
| 5,814,516 A * | 9/1998 | Vo-Dinh | 356/301 |
| 5,995,236 A * | 11/1999 | Roth et al. | 356/445 |
| 7,141,212 B2 * | 11/2006 | Catt et al. | 356/440 |
| 7,492,461 B2 | 2/2009 | Hebert et al. | |

* cited by examiner

*Primary Examiner* — Gregory J Toatley
*Assistant Examiner* — Juan D Valentin
(74) *Attorney, Agent, or Firm* — Lerner, David, Littenberg, Krumholz & Mentlik, LLP

(57) ABSTRACT

The present invention provides an optics assembly, a reflectometer, and a diagnostic device for providing quantitative measurement of optical radiation reflected from a sampling area on an assay matrix. The reflectometer includes an optical radiation source and a detector. The optical radiation source and the detector are mounted in a single plane. An optics assembly is configured to direct the illumination from the optical radiation source to the sampling area on the assay matrix and to direct the radiation diffusely reflected from the sampling area to the detector. The optics assembly is positioned over the face of the circuit board having the optical radiation source and detector mounted directly thereto. The present invention also provides a method for determining the presence of one or more selected analytes in a sample employing a plurality of sampling areas on one or more assay matrixes.

8 Claims, 8 Drawing Sheets

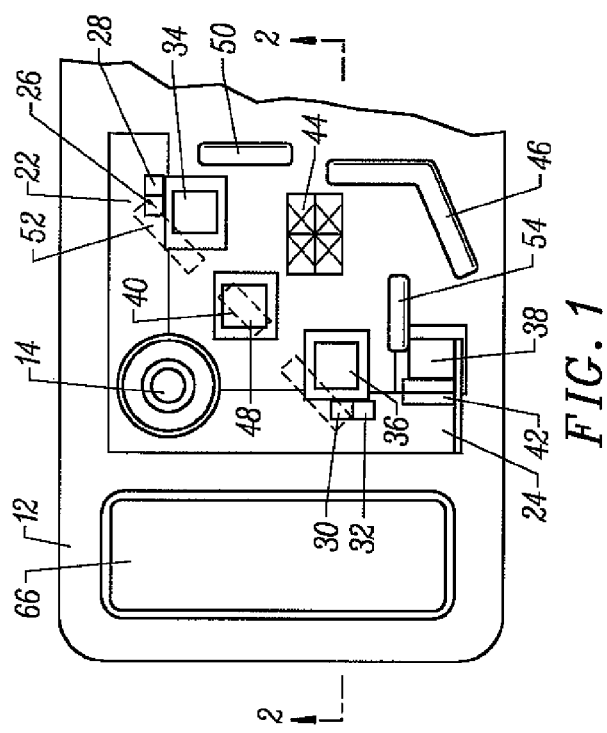

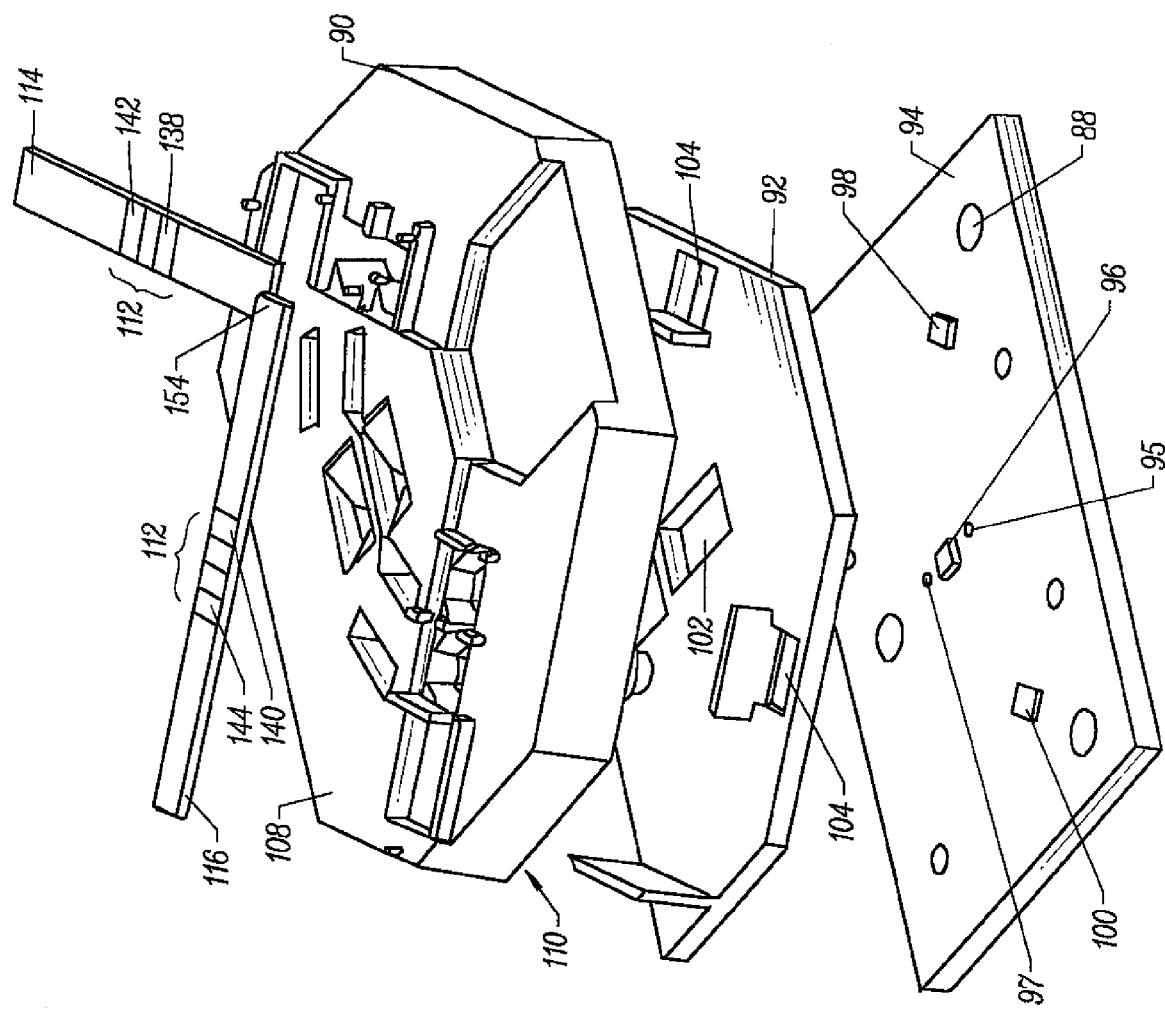

METHOD AND DEVICE FOR MEASURING REFLECTED OPTICAL RADIATION

CROSS-REFERENCE TO PRIORITY APPLICATIONS

This application claims the priority to and the benefit of U.S. patent application Ser. No. 11/188,079, filed Jul. 21, 2005, which is a continuation of U.S. patent application Ser. No. 08/642,228, filed Apr. 30, 1996, now abandoned.

RELATED APPLICATION

The subject matter of this application is related to a disposable single-use digital electronic instrument that is entirely self-contained, including all chemistry reagents, as disclosed in U.S. application Ser. No. 08/111,347 entitled "Novel Disposable Electronic Assay Device" filed Aug. 24, 1993 by Michael P. Allen and now abandoned, U.S. application Ser. No. 08/455,236 entitled "Novel Disposable Electronic Assay Device" filed May 31, 1995 by Michael P. Allen, and U.S. application Ser. No. 08/512,844 entitled "Dry Reagent Particle Assay And Device Having Multiple Test Zones And Method Therefore" filed Aug. 9, 1995 by Joel M. Blatt and Michael P. Allen. The above applications have the same assignee as the present invention and are incorporated herein by reference in their entirety.

FIELD OF THE INVENTION

The present invention relates to a method and device for precisely measuring optical radiation reflected from a surface, preferably a sample-exposed analytical chemistry strip in a single-use diagnostic device which displays medical information.

BACKGROUND OF THE INVENTION

Several qualitative and quantitative diagnostic tests have developed in the clinical field utilizing a reflectometer for measuring optical radiation reflected from a test element. Reflectometers have been constructed featuring optical arrangements of lenses, filters, apertures, a radiation source, and detector. Examples are described in U.S. Pat. Nos. 4,219,529, 4,224,032 and 3,536,927. In such arrangements, the separate components of the reflectometer must be accurately positioned and mounted to insure proper light path alignment and focusing. Often, problems arise with initially positioning and subsequently maintaining the proper mounting as the reflectometer is transported and operated. Furthermore, no provision is made to exclude the detection of specular reflectance which represents a significant noise factor when highly accurate and precise measurements of a selected analyte in a sample is needed.

One reflectometer devised to avoid these problems is disclosed in U.S. Pat. No. 4,518,259 to Ward. A one-piece molded housing contains a radiation guide and a source means and detector means to detect reflectance from a test element which is removably positioned on the outside of the housing. The measured reflectance is substantially free of specular component. However, the optical arrangement requires that the detector be positioned directly opposite the supported test element.

Recent emphasis has been placed upon diagnostic devices which are portable for use in clinical environment or directly by the patient. Portability requires more than being just lightweight or small, the bulk and shape should be convenient to carry and use. A reflectometer for such a device must be sufficiently compact. One example is the reflectometer disclosed in U.S. Pat. No. 4,552,458 to Lowne which supports and positions a test element in a predetermined, generally horizontal plane to avoid run off of the sample into the reflectometer. Light is reflected from a source to the test sample along a first path. From the test sample, the diffusely reflecting light is directed to a detector along a second path. The first and second paths must not lie in a common plane.

In addition to the space restriction, a single-use diagnostic device needs a reflectometer which is also inexpensive to manufacture since the device is disposable. The reflectometer may also be needed to perform a simultaneous analysis on more than one diagnostic assay or more than one test area or both. Even a reusable reflectometer may be needed to perform analysis on more than one test or sampling area using the same components. These needs have not been filled by the prior art.

Thus, a need exists in the field of diagnostics for a method and device for measurement of optical radiation which is sufficiently inexpensive, timely, efficient, durable, and reliable for use in a diagnostic device which permits point-of-care use by untrained individuals in locations such as the home, sites of medical emergencies, or locations other than a clinic. Whether the device is disposable or reusable, there is also a need to operate one or more channels simultaneously and reuse the same components for multiple test or sampling areas.

SUMMARY OF THE INVENTION

The present invention provides an optics assembly for a reflectometer which provides quantitative measurement of optical radiation from an optical radiation source diffusely reflected from within the boundaries of a detection zone on an assay matrix to the corresponding boundaries of a detector. The optics assembly includes a support having optics which image the detection zone onto the detector to define the boundaries of the detection zone by the boundaries of the detector.

Another embodiment of the inventive optics assembly is for a reflectometer which provides quantitative measurement of optical radiation from an optical radiation source reflected from a sampling area on an assay matrix to a detector. The optics assembly includes a generally planar support having at least a top and bottom face. The bottom face of the support is configured to receive illumination from the optical radiation source and transmit reflected optical radiation to the detector. The top face of the support is configured to transmit illumination directed to the sampling area and receive reflected optical radiation from the sampling area. The top face is configured to support at least one assay matrix thereon. A plurality of optics is integrally formed with the generally planar support. The plurality of optics is configured to direct the illumination from the optical radiation source entering the bottom face of the support to the sampling area on the top face of the support and to direct the radiation reflected from the sampling area through the top face and bottom face of the support to the detector.

The present invention also includes a reflectometer for providing quantitative measurement of optical radiation reflected from a sampling area on an assay matrix. The reflectometer includes an optical radiation source and a detector. The optical radiation source and the detector are mounted in a single plane.—An optics assembly is configured to direct the illumination from the optical radiation source to the sampling area on the assay matrix and to direct the radiation diffusely reflected from the sampling area to the detector. The optics assembly is positioned over the face of the circuit board having the optical radiation source and detector mounted directly thereto.

The present invention further provides a diagnostic device for providing quantitative measurement of a sample using reflected optical radiation. The device includes a housing having an exterior surface and sealing an interior area. A receptor is configured to receive the sample containing an analyte selected for determining its presence. The receptor is located on the exterior surface of the housing. At least one assay strip reacts with the sample with a self-contained reagent to yield a physically detectable change in a sampling area which correlates with the amount of selected analyte in the sample. An optical radiation source and a detector are mounted in a single plane. An optics assembly is configured to direct the illumination from the optical radiation source to the sampling area on the assay matrix and to direct the radiation reflected from the sampling area to the detector. The optics assembly is positioned over the face of the circuit board having the optical radiation source and detector mounted directly thereto.

The present invention also includes a method of determining the presence of one or more selected analytes in a sample. The method comprising the steps of introducing the sample to a sample receptor site on an assay matrix; chemically reacting the sample with at least one reagent on the assay matrix to produce a reaction product mixture corresponding to the reagent; transporting at least a portion of the reaction product mixture to a detection zone on the assay matrix; producing a physically detectable change in the detection zone which correlates with the amount of the corresponding selected analyte in the sample; directing the illumination from an optical radiation source to the detection zone; and, directing the radiation reflected from the detection zone to a detector which correlates with the amount of the corresponding selected analyte in the sample.

The present invention further provides a method for determining the presence of one or more selected analytes in a sample employing a plurality of sampling areas on one or more assay matrixes. The method includes the steps of: directing the illumination from an optical radiation source to the plurality of sampling areas and to direct the radiation reflected from the plurality of sampling areas to the detector; exposing each sampling area to optical radiation; and, measuring reflectance of the optical radiation from each sampling area with less detectors than sampling areas.

Accordingly, the present invention provides a reflectometer which is sufficiently compact and inexpensive for use in a diagnostic device that is portable and disposable after a single use—The reflectometer also provides for simultaneous analysis of multiple assays within a diagnostic device using precise and accurate measurement of the reaction chemistry of the diagnostic device with results provided in a timely manner for the convenience of the user.

The present invention also provides an optics assembly which uses fewer optical radiation sources or detectors, or both, than the number of sampling areas measured. The optics assembly also provides for the positioning of the optical radiation sources and the detectors in one plane separate from the position of the assay reaction chemistry.

The advantages, embodiments, variations and the like will be apparent to those skilled-in-the-art from the present specification taken with the accompanying drawings and appended claims.

BRIEF DESCRIPTION OF THE DRAWINGS

In the drawings, which comprise a portion of this disclosure:

FIG. 1 is a partial top plan view of a diagnostic device having a portion cut-away to view the illumination and detection optics of the present invention;

FIG. 2 is a partial cross-sectional view of the diagnostic device illustrated in FIG. 1 along the lines 2-2;

FIG. 3 is an isolated cross-sectional view of the device near the LED illustrated in FIG. 2;

FIG. 4 is an isolated cross-sectional view of the device near the detector illustrated in FIG. 2;

FIG. 5 is an exploded perspective view of a preferred embodiment of the internal assembly of a diagnostic device provided by the present invention with two assay strips, an optics assembly, shield, and printed circuit board;

DESCRIPTION OF THE PREFERRED EMBODIMENTS

Figure 6:
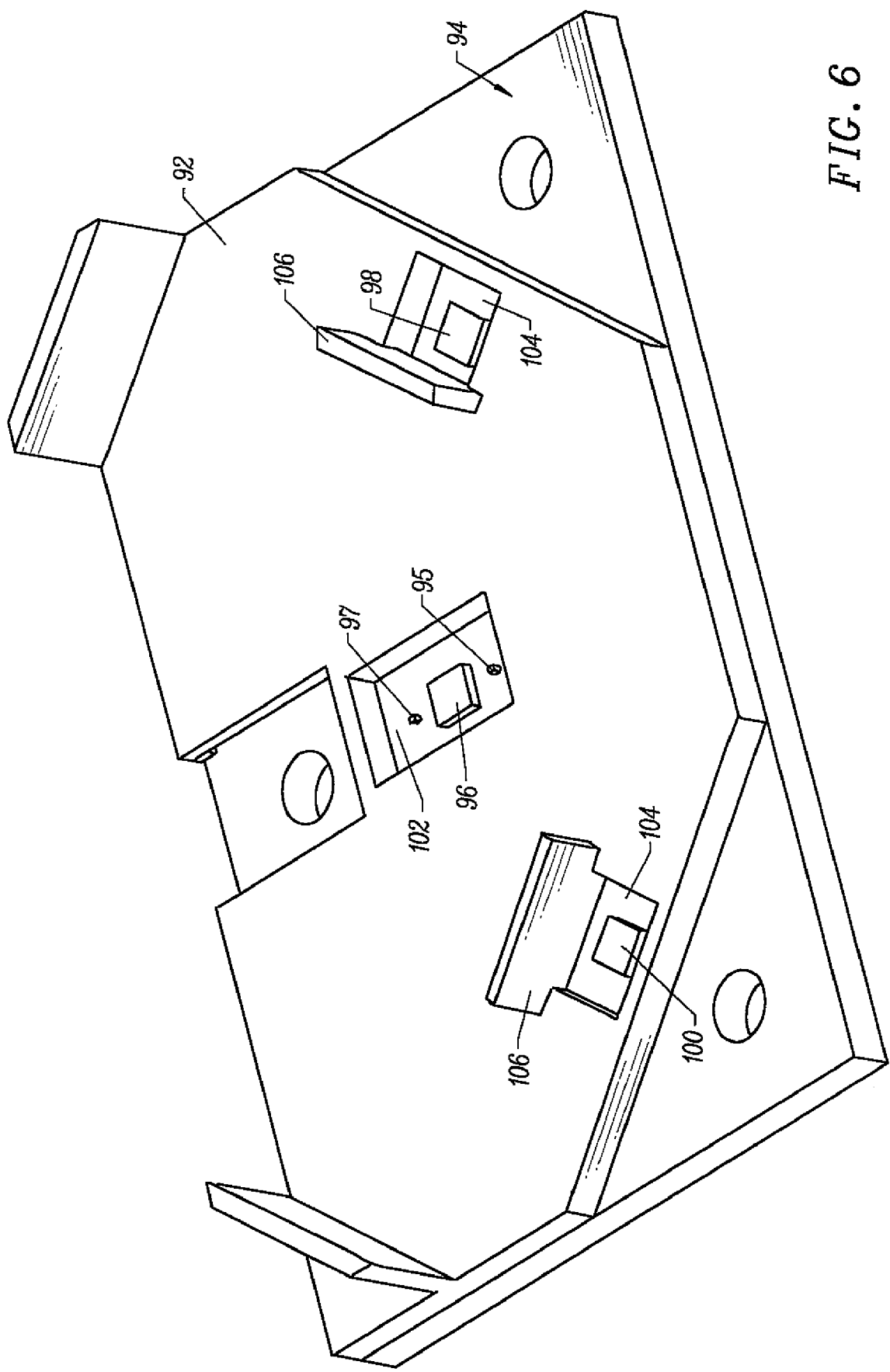
FIG. 6 is a top perspective view of the printed circuit board and shield assembled together.

The present invention is preferably utilized in the disposable, single-use digital electronic instrument and assay devices described in detail in the above-identified patent applications previously incorporated by reference. However, the present invention can also be used in multiple-use or reusable devices which are compact for hand-held operation or easy portability. The present invention provides for the precise and accurate measurement of optical radiation reflected from one or more sampling areas located on one or more assay strips to quantitatively or qualitatively determine the presence or one or more selected analytes in a sample. The sampling areas can be one or more detection zones exhibiting a physically detectable change corresponding to the amount of the selected analyte or a reference zone which provides a control for comparison to the detection zone.

One embodiment of a single-use diagnostic device 10 of the present invention is illustrated in FIGS. 1 and 2. The device 10 includes a housing 12 having a receptor such as an inlet port 14 which extends from the surface 16 of the housing to its interior 18 for receiving a sample 20 containing the one or more analytes to be determined. The inlet port 14 allows the sample 20 to be introduced to a first 22 and second assay strip 24 containing chemical reagents for determining the presence of one or more selected analytes in the sample 20.

Once the sample 20 is introduced to both the first 22 and second 24 assay strips through the inlet port 14, the sample 20 is chemically reacted with at least one reagent on each of the assay strips 22, 24 to produce a reaction product mixture corresponding to the reagent. A portion of the reaction product mixture is transported to at least one detection zone on each of the assay strips 22, 24 and produces a physically detectable change which correlates with the amount of the corresponding selected analyte in the sample 20.

As specifically illustrated in FIG. 1, each of the first 22 and second 24 assay strips contains two detection zones 26, 28 and 30, 32 respectively. A first detector 34 is positioned to measure optical radiation reflected from the detection zones 26, 28 on the first assay strip. A second detector 36 is positioned to measure optical radiation reflected from the detection zones 30, 32 on the second assay strip. A third detector 38 is positioned along the second assay strip 24 as a quality control check that an adequate quantity of sample 20 has been transported or flowed to the detection zones 30, 32. A reference detector 40 is positioned to measure the level of illumination emitted from LED 44 and provide a control for the reflected optical radiation measured at the detection or quality control zones. The quality control zone 42 does not exhibit the physically detectable change measured in each of the detection zones. Each of the detection zones and the quality control zone are examples of different types of sampling areas on the assay strips where reflected optical radiation is sampled and measured by one of the detectors.

A light-emitting diode (LED) 44 provides a source of optical radiation which is directed to each detection zone 26, 28 and 30, 32 and the quality control zone 42 by a plurality of totally internal-reflecting elements (TIR) 46 which act as mirrors and as a consequence of the refractive index of the transparent material from which they are formed, require no reflective coating.

The illumination from the LED 44 is split four ways. A part of the illumination is directed to the reference detector 40 from the reflecting element 48. Another part of the illumination is directed to detection zones 26, 28 from a series of reflecting elements 50, 52. The illumination is also directed to detection zones 30, 32 from a series of reflecting elements 54, 56. The reflecting element 46 illuminates another sampling area on the second assay strip 24 for the third detector 38.

FIG. 2 specifically illustrates another view of the device with an optics assembly 58 and printed circuit board (PCB) 60 disposed within the interior 18 of the housing. The inlet port 14 leads to the first 22 and second 24 assay strips which are supported on the optics assembly 58. Each of the detectors 34, 36, 38, 40 and the LED 44 are mounted directly to the PCB 60. A liquid crystal display (LCD) 62 is also located on the PCB 60 and is positioned to direct its display through a window 64 or opening in the exterior of the housing 12. The LED 44, each of the detectors 36, and the LCD 62 are connected through the PCB 60. A pocket of desiccant 66 can be provided to prevent moisture from affecting the shelf life stability or the operation of the device 10.

FIG. 3 isolates a portion of the optics assembly 58 surrounding the LED 62 to illustrate one embodiment for splitting the optical radiation emitted from the LED 62 into multiple light paths to be directed to sampling areas on the first 22 and second 24 assay strips. The illumination emitted from the LED 62 indicated by the arrows 68 passes through a portion of the optics assembly formed as an aspheric collimator 70. A four-way pyramidal TIR mirror 72 partially collimates the surface emissions into the optics assembly 58 as indicated by arrows 74. An edge trap 76 deflects edge emissions as indicated arrows 78.

FIG. 4 isolates another portion of the optics assembly 58 of the device which focuses each of the multiple light paths to illuminate a specific detection zone such as 36 on the second assay strip 24 and collect off-axis backscatter of the reflected light. The partially collimated surface emissions indicated by the arrows 74 are focused by a TIR prism 80 onto one of the detection zones 30 on the second assay strip. The backscattered radiation from the detection zone 30 indicated by the arrows 82 is focused by a torroidal concentrator lens 84 onto the respective detector 36.

In a preferred embodiment illustrated in FIG. 5, a reflectometer 86 includes a PCB 88, an optics assembly 90, and a shield 92. The PCB 88 has one face 94 with a reference detector 96 and zone detectors 98, 100 mounted directly thereto. The face 94 of the PCB also has two LEDs 95, 97, one for each channel of illumination, mounted directly to the PCB. As will be discussed in more detail below, the LEDs 95, 97 are a bare die form without an integral lens, enclosure, or housing. As a result, the LEDs 95, 97 provide illumination in all directions above the face 94 and is directed only by the optics assembly 90. Similarly, the zone detectors 98, 100 and reference detector 96 are bare die mounted directly to the face 94 of the PCB. The LEDs 95, 97 and the detectors 96, 98, 100 are all positioned in the same plane.

FIG. 6 illustrates the position of the shield 92 over the PCB 88. Aperture 102 is provided through the shield 92 to prevent obstructing the LEDs 95, 97 and the reference detector 96. Openings 104 are provided to prevent obstructing zone detectors 98, 100. The shield 92 includes upstanding walls 106 which prevents stray radiation from entering the zone detectors 98, 100. The upstanding walls 106 are positioned adjacent the reflecting and refracting elements of the optics assembly 90 when the reflectometer 86 is fully assembled.

Figure 7:
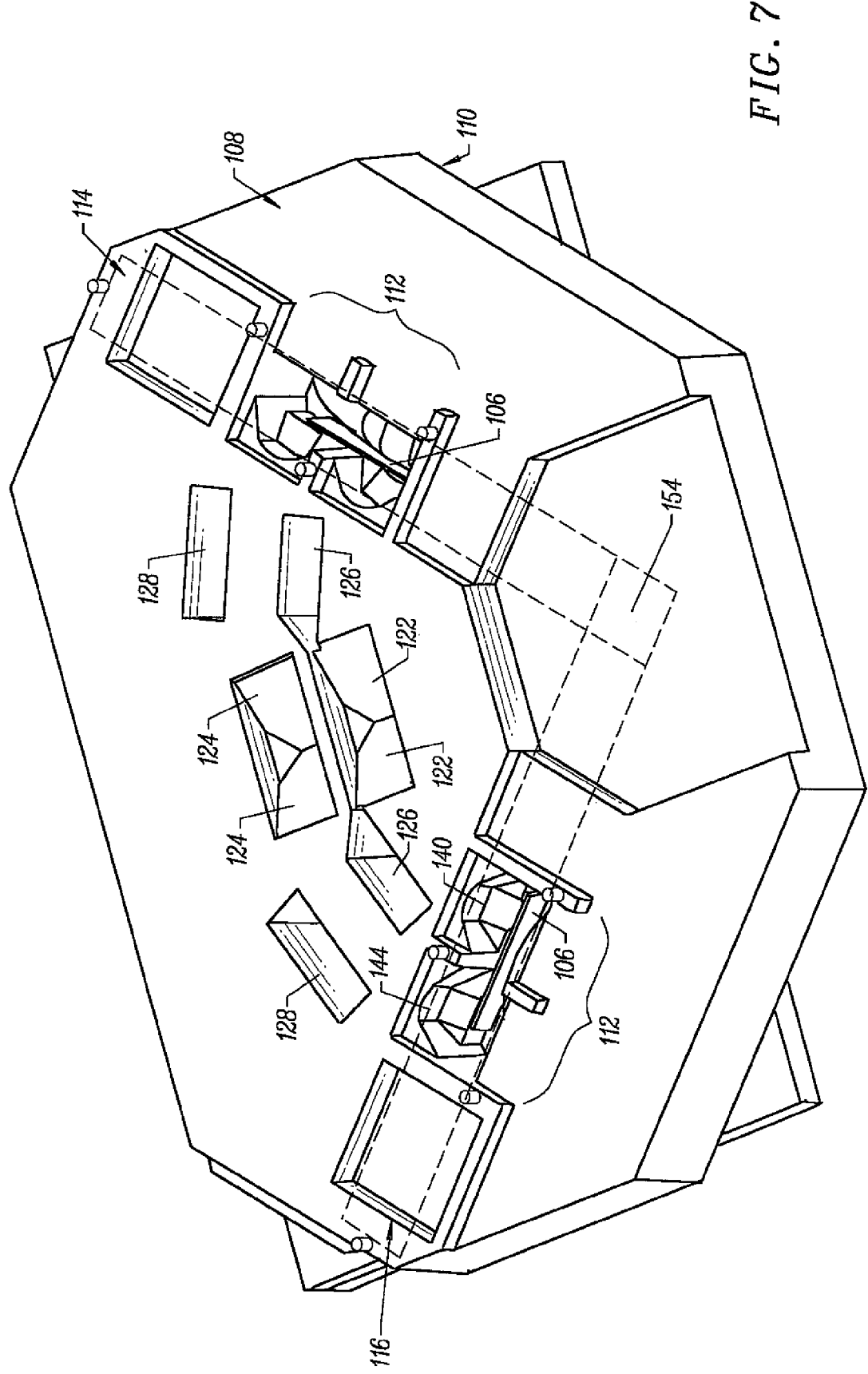
FIG. 7 is a top perspective view of the optics assembly plane in FIG. 5 with two assay strips shown in phantom to indicated their position relative to the illumination and detection optics.

FIG. 7 illustrates the positions of the PCB 88, the optics assembly 90, and the shield 92 when assembled. The optics assembly 90 is a generally planar support having at least a top face 108 and a bottom face 110. The bottom face 110 is configured to receive illumination from the LEDs 95-97 and the optics assembly 90 directs the illumination to one or more sampling areas 112 on a first 114 and second 116 assay strip illustrated in phantom. The top face 108 of the optics assembly is also configured to transmit the diffusely reflected optical radiation returning from the sampling areas 112 to one or more of the zone detectors 98, 100.

The top face 108 of the optics assembly is configured to transmit illumination directed toward the sampling areas 112 on the first 114 and second 116 assay strips. The top face 108 also transmits the optical radiation diffusely reflected from the sampling areas 112 to one or more of the zone detectors 98, 100. The top face 108 also supports and positions the first 114 and second 116 assay strips as illustrated in phantom.

Figure 8:
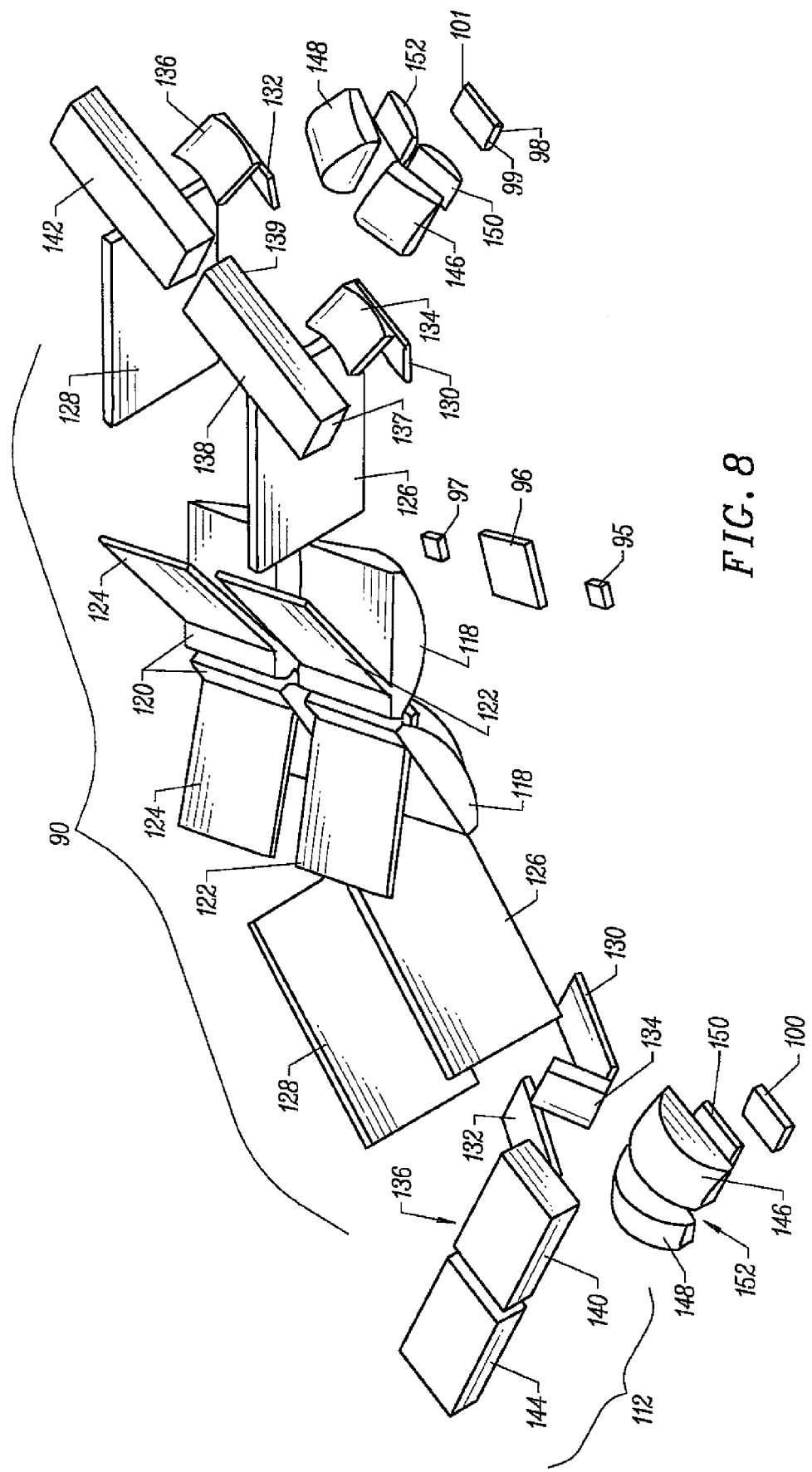
FIG. 8 is an isolated perspective view of the illumination and detection optical elements of the of the optics assembly and the LEDs and detectors as in FIG. 5.

The discrete light paths or channels are illustrated with more clarity by isolating the detectors, the LEDs, and the optics without the surrounding plastic in FIG. 8. The illumination from each LED 95, 97 located underneath the optics assembly 90 is partially collimated by respective pairs of refracting elements 118, 120. Stray illumination off of the surface of reflecting elements from each LED 95, 97 is directed to reference detector 96'. The partially collimated illumination is split into two channels for each pair of refracting elements 118, 120 for a total of two pairs of channels or four individual channels of illumination. Each pair of channels is then deflected off a series of reflecting element pairs in the following sequence: pairs of reflecting elements 122 and 124, pairs of reflecting elements 126 and 128, and pairs of reflecting elements 130 and 132.

The illumination of each channel is then passed through pairs of refracting elements 134 and 136 which spread the illumination for each channel in a predetermined shape across the sampling areas 112. More specifically, the pair of refracting elements 134 spread the illumination across first detection zones 138 and 140 on assay strips 114 and 116 respectively. The pair of refracting elements 136 spread the illumination across second detection zones 142 and 144 on assay strips 114 and 116 respectively.

The diffused optical radiation reflected downward by the first detection zones 138 and 140 is partially collimated by a pair of refracting elements 146. Similarly, the diffused optical radiation reflected downward by the second detection zones 142 and 144 is partially collimated by a pair of refracting elements 148. Pairs of refracting elements 150 and 152 further direct the partially collimated diffuse optical radiation from the refracting elements 146 and 148 to detectors 98 and 100. More specifically, detector 98 receives the diffused optical radiation from the first and second detection zones 138, 142 on the first assay strip 114. Detector 100 receives the diffused optical radiation from the first and second detection zones 140, 144 on the second assay strip 116.

Each pair of refracting elements such as 146 and 150 used for detection zone 138 constitutes an anamorphic lens system which can differentially image the detector zone 138 onto the detector 98 so that the boundaries of detector 98 clearly define boundaries of detection zone 138 in each axis independently. The leading edge 99 and the trailing edge 101 of the detector 98 define the leading edge 137 and the trailing edge 139 of the detection zone 138 with regard to the placement of the chemical reagents on the assay strip 114. The anamorphic lens system is designed to accommodate placement tolerance of the detector die 98 and the LED dies 95 and 97 by differentially magnifying the detection zone 138 onto the detector 98 through anamorphic refractive elements 146 and 150 such that the illumination zone overfills the detection zone 138 in the direction of sample flow and underfills perpendicularly to the direction of sample flow. Furthermore, the present invention intends to provide uniformity of sensitivity throughout the detection zone 138.

Both the illumination optics and the detection optics have a common field of view at the optical sampling area. It is preferred to have only one of the optics define the actual size of the optical sampling zone while the other optics overfills to encompass the defined zone. This can be accomplished in each axis independently. The illumination optics can also define the size of the optical sampling zone where power transfer efficiency and precision of registration are primary concerns. The detector size can be selected so that all the light collected by the lens falls within the boundaries of the detector. The placement of the detector on the PCB is less critical, but the design of the illumination optics must achieve the predetermined resolution and uniformity.

A rectangular detector chip should be used to define the optical sample zone when imaged onto the sample where uniformity of response is the primary concern. The illumination then overfills the optical sample zone. The position of the optical sampling zone on the detection zone is determined by the optically leveraged image of the detector location on the PCB which is not usually as well-controlled as the molding of the optical components.

The present invention also provides for a hybrid arrangement. The illumination optics can define the optical sample zone while the detection optics defines the optical sample zone in the other axis.

Of the light that is delivered to the optical sampling zone c and is within the field of view of the detector and its lens, only a small portion of the backscatter is collected by the lens and transferred to the detector. The lower the lens f/number, the greater the collected energy but the shallower the depth of field. Using aspheric profiles on the lens, a fairly low f/number can be achieved with good resolution. If the lens is off/axis and the device is using the detector to define the optics sampling zone, however, a higher f/number may be used to achieve the desired resolution off-axis.

Avoiding the specular component of the reflected energy is accomplished by considering three main factors in designing the collection lens aperture and selecting position of the lens in the light path. These factors include the specular scattering angle of the substrate material, the added dispersion due to the illumination optics design, and the field of view of the collection lens.

The refracting elements or lenses used in the embodiments of the present invention are preferably made of styrene, although acrylic plastic materials are also suitable. The lens does not have to be round and can have different f/numbers in each axis. For example, the lens can have a low f/number in the aligned axis and a higher f/number in the off-axis to achieve the desired resolution over a given depth of field. This asymmetry is also helpful in avoiding the specular reflective component.

in FIG. 8, the LEDs 95, 97 and the detectors 96, 98 and 100 are positioned in the same plane. The reflecting and refracting elements of the optics assembly 90 are generally positioned in a second plane which is parallel to the plane containing the LEDs and detectors: The first and second detection zones 138, 140, 142, and 144 on the first and second assay strips 114 and 116 are positioned in a third plane adjacent and parallel to the top face 108 of the optics assembly 90 as further illustrated in FIG. 7.

FIGS. 7 and 8 also illustrate bottom face 110 of the optics assembly receiving the illumination from LEDs 95 and 97 from underneath the optics assembly. After directing the illumination off the reflecting elements and through the refracting elements described above, the top face 108 of the optics assembly transmits the illumination to the sampling areas 112 and receives the diffused optical radiation reflected from the sampling areas 112. The bottom face 110 subsequently transmits the diffused reflected optical radiation through the refracting elements to the detectors 98 and 100.

Figure 9:
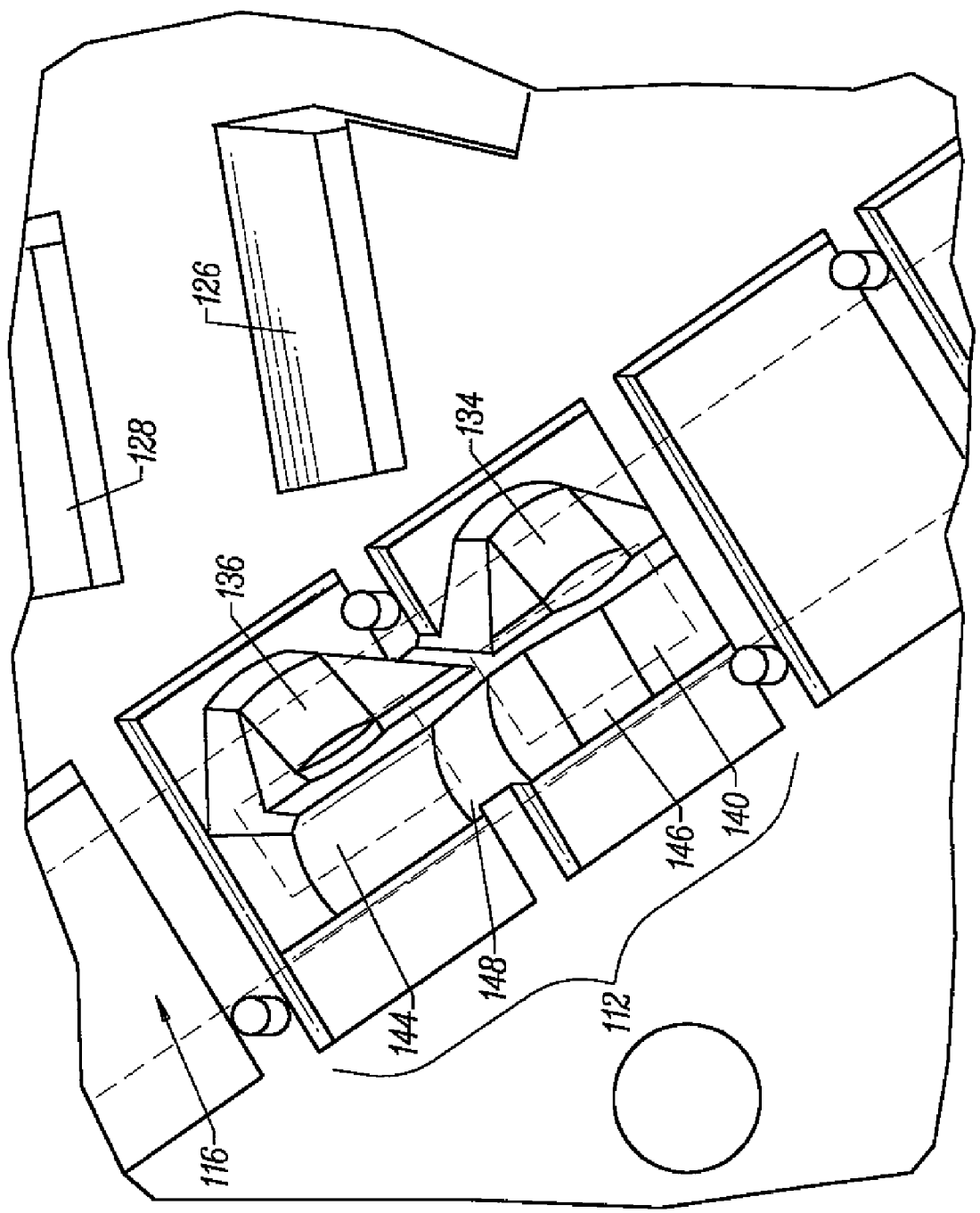
FIG. 9 is isolated top perspective view of the optics of FIG. 7 surrounding the sampling areas shown in phantom.

FIG. 9 illustrates in more detail the optics used at the sampling areas 112. One of the channels of illumination are directed off of each reflecting element 126 and 128 to the reflecting elements 130 and 132 (not shown) located underneath the refracting elements 134 and 136. Each channel of illumination is spread and shaped onto the first and second detection zones 140 and 144 (in phantom) by the refracting elements 134 and 136. The optical radiation diffusely reflected from the first and second detection zones 140 and 144 is partially collimated by refracting elements 146 and 148.

The placement of the two assay strips 114, 116 on the top face 108 of the optics assembly of the preferred embodiment is illustrated in FIG. 5 and in phantom in FIG. 7. The assay strips 114, 116 overlap at one end to form a sample receptor 154 connected to an inlet port (not shown) and are arranged at an angle to one another. A 90-degree angle is preferred for packaging compactness. The dimensions of each assay strip 114, 116 are about 30 mm by about 3 mm. Each assay strip 114, 116 has two detection zones 138, 142, and 140, 144 respectively as optical sampling areas 112 with a nominal centerline spacing of about 4 mm. The first detection zones 138 and 140 are about 12 mm from the sample receptor 154.

One preferred embodiment of a circuit and the discrete electronics which control the sequence of measuring the LED illumination with the reference detector and the reflected optical radiation from multiple detection zones is illustrated in Fig. TO. The circuit 160 integrates the process control, operator input, and reaction of the electronics. A microcontroller 162 controls the output from LEDs 95 and 97. The microcontroller 162 includes RAM memory 164 of about 64 bytes, about a 2 kilobyte ROM cache 166, a timer 168, and a central processing unit (CPU) 170. The RAM memory 164 contains spectral output characteristics and codes which identify the manufacturing lot numbers of the device components. The ROM cache 166 contains a program which includes, but is not limited to, interpreting the voltage off the detectors and reference detector, relating the signal strength ratio to the reference strength, providing results in terms of analyte concentration, trapping errors and performing other quality control checks. The microcontroller 162 selects the sequence of inputs from detectors 96, 98, and 100.

An analog ASIC 172 includes a multiplexer 174 used to integrate the signal from the detectors 96, 98, and 100. The CPU 170 is used to count the time required for the integral to reach a fixed voltage comparator threshold. The time is proportional to the average signal over the sampling period. A voltage converter 176 converts the analog signal from the detectors 96, 98, and 100 to a digital signal. The converter 176 provides a multiplexed, digital signal to the microcontroller 162.

The microcontroller 162 preferably includes a serial port 178 for the programming of information into the microcontroller 162 or the download of information collected from the assays to auxiliary equipment. The output from the assays is displayed by a 3^ digit liquid crystal display 180. A start switch 182 can manually control the microcontroller 162 functions. An oscillator 184 provides a time base for the microcontroller 162.

The power needed by the microcontroller 162 and other components is provided by two batteries 186.

The microcontroller 162 controls the entire operation of the device including, but not limited to, turning on the device in response to opening the device's packaging or other event; timing, recording, and processing the instrument zero function; controlling any time delays or adjusting the timing and quantity of reading one or more of the sampling areas; determining when the reaction has stabilized and was completed within the appropriate criteria such as time, temperature, etc.

Figure 11:
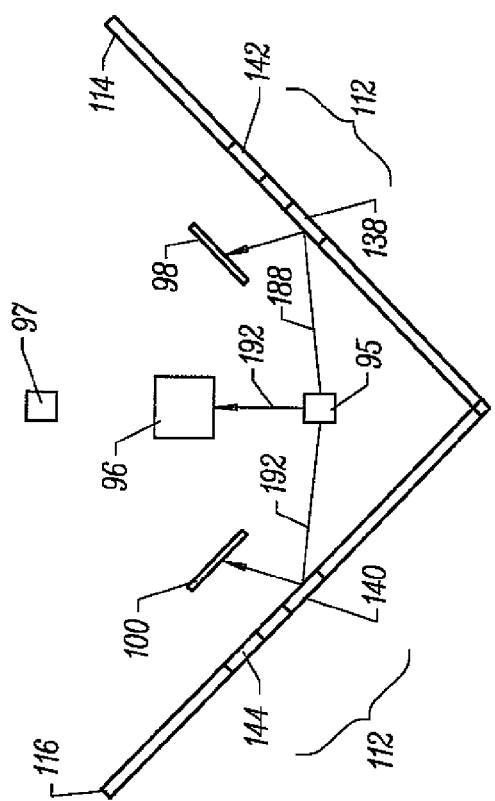
FIG. 11 is a simplified representation of the optics for a first illumination source for measuring optical radiation diffusely reflected from multiple detection zones using one detector per assay strip.
Figure 12:
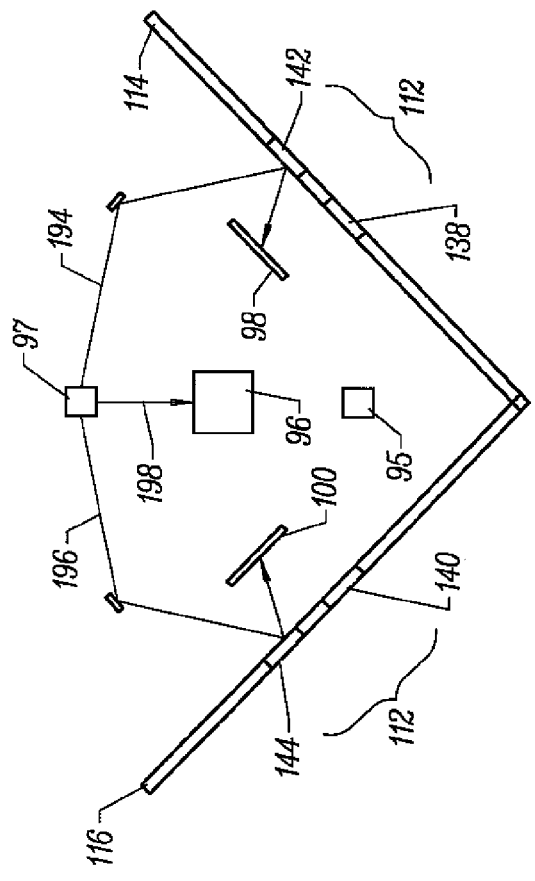
FIG. 12 is a simplified representation of the optics as in FIG. 11 with a second illumination source for measuring optical radiation diffusely reflected from multiple detection zones using one detector per assay strip.

The operation of the circuit 160 is illustrated in FIGS. 11 and 12 using simplified representations of the optics to emphasize alternating the use of one detector with two illumination sources for measuring optical radiation diffusely reflected from multiple sampling areas. During a first sequential mode seen in FIG. 11, the circuit 160 turns on LED 95 providing illumination which is partially collimated and directed into two channels 188 and 190. The two channels 188 and 190 are directed by the reflecting and refracting elements described above to the first detection zones 138 and 140 of the first and second assay strips 114 and 116. The optical radiation diffusely reflected from the first detection zones 138 and 140 is directed by the refracting elements to detectors 98 and 100 respectively. Simultaneously, the reference detector 96 measures stray illumination 192 off of the refracting elements to determine the relative intensity of LED 95 and provide a control loop to regulate the intensity of the LED electronically. The circuit 160 correlates the measurements from detectors 96, 98, and 100 with LED 95.

During a second sequential mode seen in FIG. 12, the circuit 160 turns on LED 97 providing illumination which is partially collimated and directed into two channels 194 and 196. The two channels 194 and 196 are directed by the reflecting and refracting elements described above to the second detection zones 142 and 144 of the first and second assay strips 114 and 116. The optical radiation diffusely reflected from the second detection zones 142 and 144 is directed by the refracting elements to detectors 98 and 100 respectively. Simultaneously, the reference detector 96 measures stray illumination 198 off of the refracting elements to determine the relative intensity of LED 97. The circuit 160 correlates the measurements from detectors 96, 98, and 100 with LED 97.

As a result, the circuit 160 can compare the measurements of the first and second detection zones on each assay strip 114, 116. Using these measurements with information stored in the microprocessor 162 accurate results upon completion of each assay. Examples of the information stored in the microprocessor includes, but is not limited to, algorithms or calibration curves for the analytes selected for analysis and other assay calibration information; reaction stabilization, end-point, or rate information; and manufacturing lot information on each of the chemical reagents, detectors, LEDs, assay strips, and other components used in the device.

There are a number of convention LEDs commercially available which are suitable for use with the present invention. Preferably, the LED is a bare dye form without any housing, enclosure, or lens so that the LED can be mounted directly to the PCB with great precision and reproducibility.

Several commercially available detectors are suitable for use with the present invention. Preferably, a silicon detector has wavelength sensitivity characteristics which are broadly applicable. One such detector is the Siemens BPW34 which uses a silicon detector. The silicon detector has a small-signal linearity and thermal stability in the photocurrent mode which minimizes differential channel-to-channel errors. Although the sensitivity is highest for near-infrared wavelengths, it has a wide spectral response for operating with a wide variety of LEDs. As with the LED, the present invention prefers to mount the detector die directly to the PCB. Thus, the detector should be free of any housing, enclosure, or lens.

The transfer of optical power from the LED to the detector involves several factors such as the directional radiation pattern of the LED, the ability of the illumination optics to capture and deliver the radiation to the detection zone, the reflectance and scattering pattern of the detection zone, the ability of the collection optics to capture and deliver the reflected radiation to the detector, and the detector's directional sensitivity. A preferred Mitsubishi MCR2N LED and Siemens BPW34 detector typically have a radiation or sensitivity pattern that varies with cosinell of the angle from normal incidence. The Siemens BPW34 has a Lambertian response (n=1, like the reflectivity of the nylon substrate) while the emitter fits a cosine4 characteristic.

The transfer efficiency of the illumination optics in the preferred embodiment is about 28% which demonstrates that about 28% of the radiation emitted from the LED is delivered by each illuminating optics arm to the sampling area. By comparison to the prior art, this is a substantial increase in transfer efficiency. Furthermore, about 0.84% of the light emitted by the LED reached the detector for the optics sampling area with 80% common fields of view.

The current transfer efficiency of the Mitsubishi MCR2N and Siemens BPW34 is calculated using the 0.4 to 1.8 mw output range from a drive current of 20 ma for the LED and a sensitivity of the detector at 660 nm. The overall system current transfer efficiency from the LED driver through the detector output is about 75.6 na/ma. For every milliamp of LED drive current, the detector will output a maximum of about 75.6 nanoamps of signal corresponding to wet unexposed nylon with an 80% common field of view.

The present invention prefers to mount the LED and detector in the same plane and provide the optics assembly to gather and direct the illumination to the detector with an appropriate series of reflecting and refracting elements. The present invention overcomes several problems in the prior art by positioning the illumination source and detector in the same plane to create a reflectometer so compact and inexpensive to manufacture that it can be used in a single-use diagnostic device.

Although two assay strips are simultaneously analyzed by the embodiments illustrated above, the present invention also provides for sequentially analyzing multiple sampling areas on one strip or for analyzing more than two strips either simultaneously or sequentially. Based upon the inventive concepts and embodiments described herein, it is within the scope of those skilled in the art to make the appropriate modifications.

Figures 10, 13:
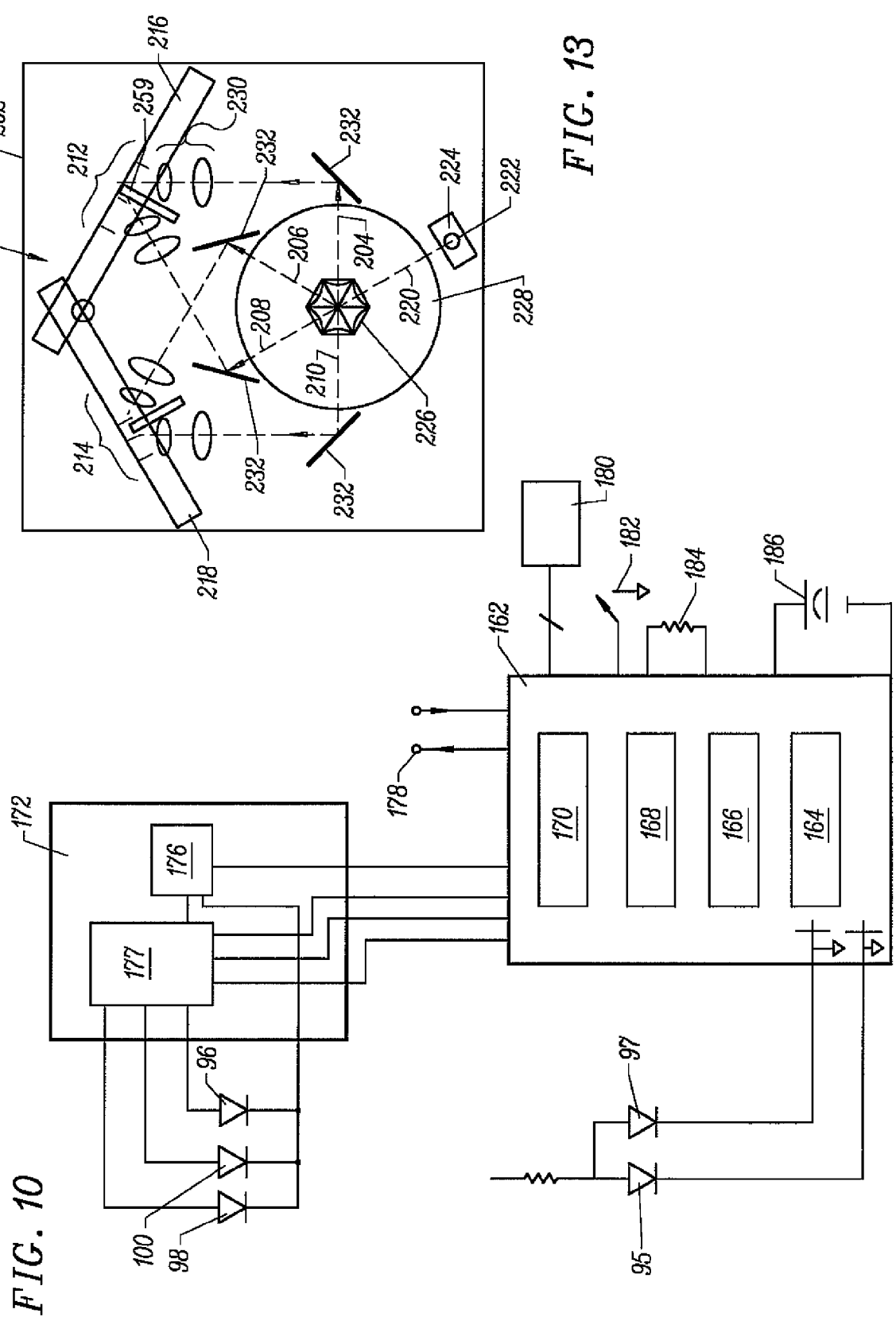
FIG. 10 is a circuit diagram of the electronics for the illumination and detection optics in the preferred embodiment.
FIG. 13 is a top plan view of an alternate embodiment of a diagnostic device for analyzing multiple assay strips using five discrete light channels and one LED.

Another embodiment of a diagnostic device of the present invention is illustrated in FIG. 13. The assay device 200 includes a housing 202 which contains therein four solid clear plastic illumination channels 204, 206, 208, 210 to separate sampling areas 212, 214 on two assay strips 216, 218. One additional clear plastic illumination channel 220 leads to a reference detector 222 off of an intermediate reflecting element 224 for subsequent measurement of the LED intensity. The captured LED radiation is nominally collimated by two elements. One element is a cylindrical entry lens 226 which is part of the beamsplitting cluster immediately above the LED chip (not shown). The other element is a segment of a reflective axicon 228 on-axis to the chip. The semi-collimated radiation is directed through a pre-determined length of acrylic channel to receptor elements 230 at the opposite end. The receptor elements 230 have a reflective aspheric cylindrical element and an aspheric toroidal lens to direct and focus the radiation onto the sampling area. Intermediate TIR mirror elements 232 appropriately redirect each path. Preferably, each of the reflective elements are TIR mirrors.

The five channels 204, 206, 208, 210 and 220 in the device 200 are folded to access the closely adjacent detection zones in the sampling areas 212, 214 on the two assay strips. Crossover illumination from one channel to another at the sampling areas on the same assay strip are prevented by upstanding walls or baffles 259. A sixth zone represents dead space for clearing the LED's center electrode bonding wire. A hex cylindrical prism is the LED's beamsplitter which functions as the first cylindrical lens. The fifth channel 220 provides a detector control loop to regulate the intensity of the LED electronically.

In another inventive embodiment, a beam chopper can be used instead of the beam splitting cluster described in FIG. 13 to form the discrete channels 204, 206, 208, 210, and 220 in any desired sequence. This would effectively accomplish the multiplexing sequence described above and illustrated in FIGS. 11 and 12. As a result, one source of illumination or LED can be used to form multiple channels directed at multiple sampling areas 212, 214 on strips 216, 218. Independently, one or more detectors can then be used to measure the optical radiation diffusely reflected from the sampling areas 212, 214.

Figure 14:
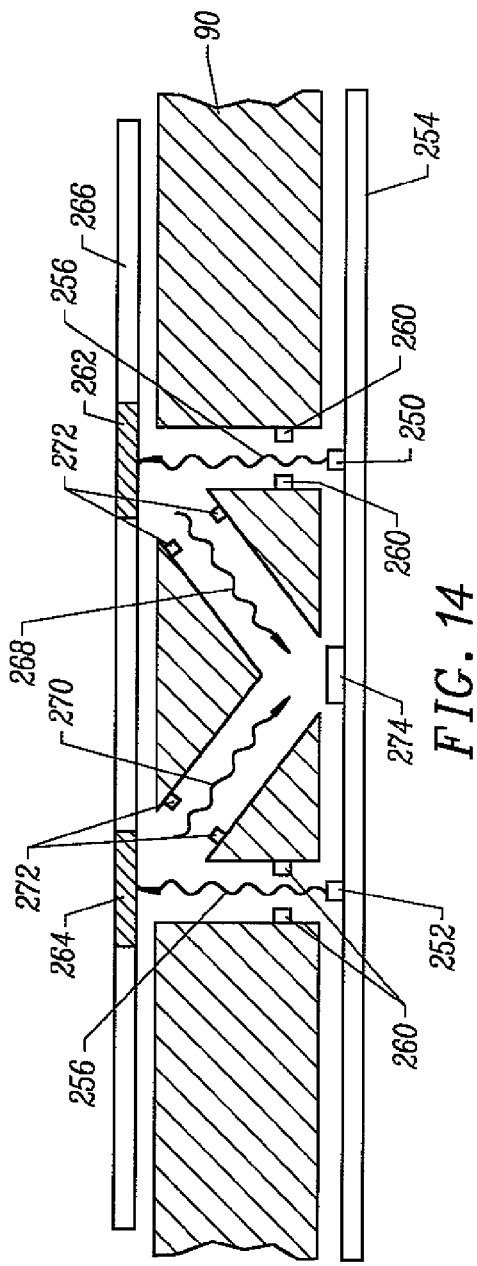
FIG. 14 is cross-sectional view of another embodiment using apertures in an optics assembly for analyzing an assay strip in a diagnostic device.

As defined herein, the optics suitable for use with the present invention include, but are not limited to, conventional reflecting and/or refracting elements and other types of optics. In addition, apertures are also suitable optics. As illustrated in FIG. 14, two bare die form LEDs 250 and 252 are directly mounted on a PCB 254. The illumination from LEDs 250, 252 are shaped into discrete channels 256, 258 by apertures 260 and directed to sampling areas 262 and 264 on an assay strip 266. The optical radiation diffusely reflected from the sampling areas 262, 264 are shaped into discrete channels 268, 270 with the assistance of apertures 272 and directed to one bare die detector 274 which is mounted directly on the PCB 254.

Other light channels such as light pipes or waveguides are suitable for use with the embodiments of the present invention. A hybrid arrangement is also suitable for use in the present invention whereby a light pipe is used on one axis and a waveguide is used on another axis.

Generally, a light pipe transmits light from one end to the other using multiple internal reflections like a fiber optic. Energy is concentrated along the path of the light pipe in a conic shape. Since the light pipe can homogenize the input radiation to a uniform output, the input optical components and alignments are less critical. The light diverges very rapidly from the output ends however, which makes it difficult to efficiently focus onto the target with small elements in a compact space to avoid specularity in detection.

A waveguide functions to control the space within the optical material to relay light rays from input to output elements to precisely control the path of light rays and can maintain image integrity. The waveguide can efficiently deliver a tight cone of radiation having a high f/number to the output elements which allows for less critical design of output elements and more control in avoiding specular radiation to the detector. The design and alignment of the input elements, however, are more important. These factors usually are well-controlled in an optical injection molding process.

Numerous modifications and variations of the present invention are possible in light of the above teachings. It is therefore to be understood that within the scope of the appended claims, the invention may be practiced otherwise than as specifically described herein.

What is claimed:

1. An assay strip meter comprising:
    at least one optical radiation emitter;
    a plurality of assay strips containing chemical reagents for detecting the presence of one or more analytes in a sample, wherein each assay strip contains a plurality of sample areas that contain a plurality of reagents that chemically react with the sample; and
    a plurality of detectors, wherein the plurality of detectors each correspond to a sampling area, at least one of said plurality of detectors corresponding to a first of said plurality of assay strips and at least a second of said plurality of detectors simultaneously corresponding to a second of said plurality of assay strips;
    a further detector, wherein the further detector corresponds to a reference area independent of the plurality of assay strips.

2. The assay strip meter of claim 1, wherein a plurality of sample-reagent mixtures are measured one of simultaneously and sequentially.

3. The assay strip meter of claim 1, wherein optical radiation emitted from the optical radiation emitter is split and directed to the plurality of sample areas and the reference area.

4. The assay strip meter of claim 3, further comprising a plurality of totally internal-reflecting elements adapted to direct the optical radiation emitted from the optical radiation emitter.

5. The assay strip meter of claim 3, wherein the optical radiation emitter is a light emitting diode.

6. The assay strip meter of claim 5, wherein the optical radiation emitted from the light emitting diode is split four ways.

7. The assay strip meter of claim 1, wherein said plurality of assay strips is two assay strips and the plurality of sample-reagent mixtures of said two assay strips are measured simultaneously.

8. The assay strip meter of claim 1, wherein the further detector provides a control for the sampling areas.

* * * * *

UNITED STATES PATENT AND TRADEMARK OFFICE
CERTIFICATE OF CORRECTION

PATENT NO. : 8,045,169 B2
APPLICATION NO. : 12/235371
DATED : October 25, 2011
INVENTOR(S) : Raymond T. Hebert, Joel M. Blatt and Joseph T. Widunas It is certified that error appears in the above-identified patent and that said Letters Patent is hereby corrected as shown below:

In the Specifications:
Column 1, line 39, "have" should read --have been--
Column 1, line 54, "is needed" should read --are needed--
Column 1, line 61, "component" should read --components--
Column 2, line 20, "which is" should read --which are--
Column 3, line 26, "comprising" should read --comprises--
Column 4, line 22, "indicated" should read --indicate--
Column 4, line 27, "is isolated" should read --is an isolated--
Column 4, line 43, "is cross-sectional" should read --is a cross-sectional--
Column 4, line 60, "or one" should read --of one--
Column 5, line 39, "and as" should read --and, as--
Column 5, line 61, "shelf life" should read --shelf-life--
Column 6, line 6, before "arrows" insert --by the--
Column 6, line 26, "is directed" should read --are directed--
Column 6, line 36, "prevents" should read --prevent--
Column 6, line 63, "off of the" should read --off the--
Column 8, line 51, "illumination are" should read --illumination is--
Column 8, line 52, "off of each" should read --off each--
Column 9, line 10, "Fig. TO" should read --FIG. 10--
Column 12, line 7, "are shaped" should read --is shaped--
Column 12, line 10, "are shaped" should read --is shaped--
Column 12, line 30, "can maintain" should read --maintain--
Column 14, line 2, "strips is" should read --strips are--

Signed and Sealed this
Seventh Day of May, 2013

Teresa Stanek Rea
*Acting Director of the United States Patent and Trademark Office*